United States Patent [19]

zur Hausen et al.

[11] 4,250,337
[45] Feb. 10, 1981

[54] TWO STAGE HYDROGENATION TO MAKE NEOPENTYL GLYCOL

[75] Inventors: Manfred zur Hausen; Manfred Kaufhold; Erhard Lange, all of Marl, Fed. Rep. of Germany

[73] Assignee: Chemische Werke Huls Aktiengesellschaft, Marl, Fed. Rep. of Germany

[21] Appl. No.: 51,321

[22] Filed: Jun. 22, 1979

[30] Foreign Application Priority Data

Jun. 24, 1978 [DE] Fed. Rep. of Germany ....... 2827795

[51] Int. Cl.$^3$ .............................................. C07C 31/20
[52] U.S. Cl. ..................................... 568/853; 568/854
[58] Field of Search ........................ 568/862, 868, 853

[56] References Cited

U.S. PATENT DOCUMENTS

| | | | |
|---|---|---|---|
| 2,400,724 | 5/1946 | Walker | 568/853 |
| 2,818,443 | 12/1957 | Roleson | 568/853 |
| 3,340,312 | 9/1967 | Duke, Jr. et al. | 568/853 |
| 3,808,280 | 4/1974 | Merger et al. | 568/853 |
| 3,920,760 | 11/1975 | Heinz | 568/853 |

FOREIGN PATENT DOCUMENTS 1219162 1/1971 United Kingdom .

OTHER PUBLICATIONS

"The Merck Index," 6th Ed., (1952), p. 441.

Primary Examiner—Joseph E. Evans
Attorney, Agent, or Firm—Millen & White

[57] ABSTRACT

In a process for the production of neopentyl glycol comprising high-pressure hydrogenating a crude hydroxypivalaldehyde, containing the monoisobutyric acid ester of neopentyl glycol as an impurity, in the liquid phase over a barium-activated copper chromite catalyst, an improvement comprises hydrogenating the crude hydroxypivalaldehyde in the presence of 3–8% of water, and in two stages, wherein, in the first stage, the temperature is 120°–160° C. and the charge of hydrogenation starting material is 0.05–1.0 liter/liter of catalyst . h., and in the second stage, the temperature is 170°–200° C. and the charge of hydrogenation starting material is 0.05–1.0 liter/liter of catalyst . h., whereby there is obtained neopentyl glycol having a degree of purity of above 98% as determined by gas chromatographic analysis.

6 Claims, No Drawings

TWO STAGE HYDROGENATION TO MAKE NEOPENTYL GLYCOL

BACKGROUND OF THE INVENTION

The present invention relates to a process for preparing pure neopentyl glycol.

The production of neopentyl glycol (NPG) is accomplished conventionally by reacting isobutyraldehyde with formaldehyde in the presence of alkaline compounds, such as alkaline solutions, alkali carbonates, tertiary amines, etc., as the catalyst. While such syntheses can be conducted without difficulty, the purification of the thus-produced NPG, contaminated by esters, is expensive from a technical and industrial viewpoint. Although processes are known wherein a relatively pure crude product is obtained, such as, for example, in processes using tertiary amines as the catalysts or operating with the addition of water-soluble alcohols in a homogeneous phase (see "Ullmanns Enzyklopaedie der technischen Chemie" [Ullmann's Encyclopedia of Technical Chemistry] 7 [1973]: 228; exact analytical data have not been divulged), these modes of operation attain their advantage of increased purity of the crude product at the cost of a considerable additional expenditure during the synthesis. The tertiary amine catalysts must first be recovered in two additional distillation stages—the first directly after the synthesis and the second stage after the hydrogenation (during which the formates are cleaved). Furthermore, an especially careful distillatory purification of the reaction products is necessary to maintain the nitrogen content thereof at a minimum level.

When a water-soluble alcohol, e.g. methanol, is used in the synthesis, its presence makes it impossible to separate the waste-water stemming from the aqueous formalin solution and the alkaline solution and/or alkali carbonate solution. For this reason, methanol and unreacted isobutyraldehyde are distilled off in additional process stages; the residue of the distillation is extracted with n-dibutyl ether; the extract is washed with water and hydrogenated; and thereafter the ether is separated by distillation.

U.S. Pat. No. 3,939,216 teaches that the reaction of isobutyraldehyde with formaldehyde can be conducted at very low expense without any problems in the presence of aqueous soda solution. However, the crude product obtained in this process contains 10–15% ester, namely, not only the hydroxypivalic acid-NPG ester, readily separable from NPG by distillation, but also —and this is not disclosed—the monoisobutyric acid-NPG ester.

This ester cannot be separated by distillation from NPG at an industrially tolerable expense. Since, heretofore, it has been possible only under extreme conditions, during which NPG is partially decomposed, to hydrogenate this ester to NPG and isobutanol, this ester constitutes the essential cause for the difficulties encountered in purifying and manufacturing NPG.

In the process described in this patent, the esters are removed by the following method:

After the hydrogenation, the esters are saponified with sodium hydroxide solution and the product is subsequently subjected to steam distillation under vacuum. This is done under maximally mild conditions at temperatures of below 140° C. and with a short residence time with the aid of a thin-film evaporator to extensively avoid NPG losses. To maintain the salts obtained in the thin-film evaporator in the fluid state, the NPG content in these salts must not drop below a certain value. Otherwise, plugging problems are encountered in the thin-film evaporator which can only be eliminated after shutdown of the apparatus by flushing with water. Due to such shutdown periods, the production capacity of the thin-film evaporator is lessened by 10-15%. For this reason, a certain quantity of NPG is allowed to remain in the waste salts, and the latter are worked up in a separate process stage. At the head of the thin-film evaporator, a dilute aqueous NPG solution is obtained from which the water is separated in a distillation stage, which consumes a large amount of energy.

Inasmuch as this mode of operation is very expensive, many attempts have been made to hydrogenate ester-containing NPG directly to pure NPG. DOS [German Unexamined Laid-Open Application] 1,804,984 (=British Pat. No. 1,219,162) proposes, as the hydrogenation catalysts, barium-activated copper chromite catalysts and temperatures of 175°–220° C.

It has been taught that hydroxypivalaldehyde can be readily hydrogenated to NPG at temperatures of below 160° C., but that temperatures of 200°–210° C. are required to reduce the esters present as impurities (British Pat. No. 1,219,162). In this process, a product was utilized which contained a small amount of ester since its manufacture was conducted with the addition of methanol (see above). Yet, these high temperatures are required to obtain low ester contents of 0.1%. The relatively low and fluctuating yields of less than 80% demonstrate that NPG was partially decomposed at the high hydrogenation temperatures.

DAS No. 2,054,601 (=U.S. Pat. No. 4,094,914) generally states that the hydrogenation of hydroaldehydes in the liquid phase is accompanied by the formation of undesirable by-products, due to long residence times required to complete the reaction, whereby the yield and purity of the diols are impaired. The effect is further aggravated by the residual alkali contents stemming from the synthesis. For this reason, this reference suggests that the hydrogenation be conducted in the gaseous phase. Here, using a nickel-containing catalyst at 128° C., a selectivity of between 98% and 99% is attained. However, the product used as the starting compound does not contain the monoisobutyric acid ester of NPG (abbreviated: MB-NPG). Therefore, this disclosure does not set forth whether, by means of this process, it is possible to solve the above-described, primary problem in NPG manufacture. Furthermore, a disadvantage inherent in this process is the high energy consumption because both the product utilized as the starting material and the required solvent must be vaporized.

All conventional processes, therefore, exhibit considerable disadvantages, in that they either avoid the formation of MB-NPG in the synthesis by special, expensive measures, or they remove this ester by alkaline saponification and then must keep the damaging effect of the sodium salts at a minimum by expensive technical, industrial installations.

SUMMARY OF THE INVENTION

Accordingly, it is an object of this invention to provide a process by means of which, at a minimum of technical, industrial expenditure, an NPG can be obtained with a degree of purity of above 98%, as determined by analysis by gas chromatography.

Upon further study of the specification and appended claims, further objects and advantages of this invention will become apparent to those skilled in the art.

These objects have been attained by providing a process for the production of NPG comprising high-pressure hydrogenating a crude hydroxypivalaldehyde, containing the monoisobutyric acid ester of NPG as an impurity, in the liquid phase over a barium-activated copper chromite catalyst, the improvement comprising hydrogenating the crude hydroxypivalaldehyde in the presence of 3–8% of water, and in two stages wherein, in the first stage, the temperature is 120°–160° C. and the charge of hydrogenation starting material is 0.05–1.0 liter/liter of catalyst.h., and in the second stage, the temperature is 170°–200° C. and the charge of hydrogenation starting material is 0.05–1.0 liter/liter of catalyst.h, whereby there is obtained neopentyl glycol having a degree of purity of above 98% as determined by gas chromatographic analysis.

DETAILED DISCUSSION

Surprisingly, it has been found that, contrary to the above-mentioned prior art prejudices, it is possible to obtain pure NPG from ester-containing crude hydroxypivalaldehyde, which contains impurities of MB-NPG and small amounts of water, by hydrogenation in the liquid phase, without the formation of by-products and without a substantial decomposition of NPG. This is accomplished by conducting the hydrogenation in two stages, namely, first at low temperatures and subsequently at higher temperatures.

Suitable catalysts employed in the process of this invention include barium-activated copper chromite catalysts, as have been suggested, for example, in U.S. Pat. No. 3,340,312. These barium-activated copper chromite catalysts are conventional [U.S. Pat. Nos. 2,137,407; 2,091,800; 2,782,243, and 2,544,771; Adkins et al, J. Am. Chem. Soc. 53, 1,091 (1931); J. Am. Chem. Soc. 53, 1,095 (1931); J. Am. Chem. Soc. 54, 1,145 (1932); Connor et al, J. Am. Chem. Soc. 54, 1,138 (1932); and Adkins et al, J. Am. Chem. Soc. 72, 2,626 (1950) whose disclaimers are incorporated by reference herein]. For example, they have the following composition: 33–35% CuO, 38% $CrO_3$, 10% BaO, as well as $SiO_2$ as the binder. These catalysts can be applied to a support. It is important that the barium-activated copper chromite catalyst be utilized in both stages. Hydrogenation in the second stage takes place satisfactorily only if the starting compound has been prehydrogenated also in the first stage according to this invention with a barium-activated copper chromite catalyst (see Comparative Example 1).

The hydrogenation problem is solved, in accordance with this invention, by hydrogenating the hydroxypivalaldehyde containing crude MG-NPG and small amounts of water in a first stage over a barium-activated copper chromite catalyst at temperatures of 120°–160° C., preferably 140°–150° C., and under a hydrogen pressure of 200–300 bar. Subsequently, in a second stage, a hydrogenation is effected over a similar or identical copper chromite catalyst at temperatures of 170°–200° C., preferably 175°–195° C., most preferably 175°–190° C., and under a hydrogen pressure of 200–300 bar.

The second stage leads to satisfactory results only by maintaining, in the first stage, the above-mentioned conditions, as well as charges of 0.05–1.0, preferably 0.1–0.5 liter of hydrogenation starting material/liter of catalyst.h. These charging conditions are also required in the second stage.

It has been found, surprisingly, that products hydrogenated in the first stage at too high a temperature or over an unsuitable catalyst are hydrogenated in the second stage only with the attendant formation of by-products and under marked decomposition to an NPG, the degree of purity of which lies below 98%. This greatly contaminated NPG cannot be further purified by distillation, although the MB-NPG content thereof, with values of 0.8–0.5%, is relatively minor (see Comparative Example 1).

It has furthermore been found that the presence of water in the crude hydroxypivalaldehyde greatly suppresses the decomposition of NPG during hydrogenation. Especially advantageous is a content of 3–8%, preferably 4.5–6.5%, which can be obtained by saturation of the organic phase with water, e.g., in following examples amounting to 4.85% and 6.12%. That is, the reaction is to be conducted in the presence of water, e.g., by adding water to the reaction mixture.

Pure NPG, for example dissolved in isobutanol, surprisingly is stable under the hydrogenation conditions only in the presence of water. Water contents of far above 8% lessen, as is known, the lifetime of the hydrogenation catalysts.

Unless otherwise specified herein, all details of the hydrogenation reactions are fully conventional as discussed, e.g., Houben Weyl, Methoden der Organischen Chemie, 4. Auflage, Band IV, Allg. Chem. Methoden, Teil 2 (1955), Georg-Thieme-Verlag Stuttgart, Seiten 283 bis 322. whose disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degree Celsius; unless otherwise indicated, all parts and percentages are by weight.

EXAMPLES

EXAMPLE 1: PRODUCTION OF CRUDE HYDROXYPIVALALDEHYDE

The present invention relates only to the hydrogenation of the crude hydroxypivalaldehyde, and not to the manufacture of the latter. In the following description, such a manufacture is described merely by way of example, as one among many possibilities.

The reaction of isobutyraldehyde with formaldehyde is conducted in an aldolizing reactor having an effective volume of 10 liters. Per hour, 16 liters of isobutyraldehyde and 8 liters of formalin (29%) are utilized. The pH is adjusted to 10.0 by the addition of 25% strength sodium hydroxide solution and automatically controlled. The reaction temperature is 60° C. The reaction product separates into two phases, the aqueous phase being discarded. The yield of crude hydroxypivalaldehyde is 80% of theory (based on formaldehyde). The product (=product A) has the following composition (calculated as devoid of isobutanol, formaldehyde, and water):

|  | % |
|---|---|
| hydroxypivalaldehyde | 65.6 |
| neopentyl glycol | 8.3 |
| acetal of isobutyraldehyde and NPG | 1.4 |
| monoisobutyric acid ester of NPG | 6.5 |
| monohydroxypivalic acid-NPG ester | 7.2 |
| 2,2,4-trimethyl-1,3-pentanediol (=TMP) | 2.8 |
| TMP monoisobutyrate | 0.2 |
| sum total of other compounds | 8.0 |

The additionally determined water content is 4.85%.

If, under otherwise unchanged conditions, the pH is set at 10.5, then the yield of crude hydroxypivalaldehyde increases to 87% of theory, based on the amount of formaldehyde employed. As for the hydrogenation, it is important that the content of esters be increased. The reaction product (=product B) has the following composition:

| hydroxypivalaldehyde | 50.8% |
|---|---|
| neopentyl glycol | 9.8% |
| acetal from isobutyraldehyde and NPG | 1.6% |
| monoisobutyric acid ester of NPG | 9.1% |
| monohydroxypivalic acid-NPG ester | 13.8% |
| 2,2,4-trimethyl-1,3-pentanediol (=TMP) | 3.4% |
| TMP monoisobutyrate | 0.2% |
| sum total of other compounds | 11.3% |

The water content, detected by another analytical method, is 6.12%.

EXAMPLE 2: 2.1: FIRST HYDROGENATION STAGE

Product A from Example 1 is hydrogenated in a high-pressure reactor having an effective volume of 28 liters (length 5 m, diameter 90 mm) and filled with 24 liters of a barium-activated copper chromite catalyst having the following composition: 33% CuO, 38% CrO₃, 10% BaO, remainder SiO$_2$ (1107 T by HARSHAW), at 145° C. and under a hydrogen pressure of 280–300 bar. Per hour, 7 liters of the isobutyraldehyde-containing aldolization product is employed, i.e. the charge is 0.292 liter of hydrogenation starting material/liter of catalyst.h. The amount of cycle gas is set at 200 Nm³/h. and the feed of fresh gas at 5–6 Nm³/h.

A sample of the hydrogenation product (=product C) is distilled for purposes of more thorough examination, at 124 mbar, and the main run, boiling between 146° and 148° C., is analyzed by gas chromatography; this run consists of:

| NPG | 96.2% |
|---|---|
| MB-NPG | 3.6% |
| 2,2,4-trimethyl-1,3-pentanediol (=TMP) | 0.2% |

The selectivity with respect to the reduction of the aldehyde-ester mixture to NPG is 97.8%. Product losses by decomposition have not occurred. The conversion of hydroxypivalaldehyde is above 99%.

When using product B from Example 1, and after an analogous conductance of the hydrogenation and the analysis of the hydrogenation product (=product D), the gas chromatogram shows the following composition:

| NPG | 93.7% |
|---|---|
| MB-NPG | 5.6% |
| 2,2,4-trimethyl-1,3-pentanediol (=TMP) | 0.3% |
| other compounds | 0.4% |

The selectivity with respect to the reduction of the aldehyde-ester mixture to NPG is 96.5%. Decomposition of the products during hydrogenation cannot be measured. The conversion of hydroxypivalaldehyde is above 99%.

2.2: SECOND HYDROGENATION STAGE

Product C (i.e. prehydrogenated product A) is hydrogenated in the same way as described in 2.1, but at elevated temperatures. The hydrogenation temperatures selected are 170°, 180°, 190°, and 200° C. The results are shown in the following table:

TABLE 1

| Hydrogenation Temperature °C. | Gas-Chromatographic Analysis of Distillate (*) (%) | | | | Ester Conversion of 2nd Stage () (%) | Yield (*) (%) |
|---|---|---|---|---|---|---|
| | NPG | MB-NPG | TMP | Residual Compounds | | |
| 170 | 98.2 | 1.2 | 0.2 | 0.4 | 66.7 | 99.9 |
| 180 | 99.3 | 0.5 | 0.2 | 0.0 | 86.1 | 99.8 |
| 190 | 99.4 | 0.5 | 0.1 | 0.0 | 86.1 | 97.5 |
| 200 | 99.6 | 0.4 | 0.0 | 0.0 | 88.9 | 71.2 |

(*)A sample of the hydrogenation product is distilled, as described in 2.1, in order to conduct an exact analysis by gas chromatography.
(**)The ester conversion of the second stage is understood to mean the following: 3.6% MB-NPG in the starting compound is reduced to 1.2% in the final product of the second stage, i.e., 2.4% is hydrogenated to NPG, i.e. a conversion of 66.7%.
(***)The yield is based on distilled product with the indicated purity.

In the same way, product D (i.e. prehydrogenated product B) is hydrogenated at the same temperatures. These results are compiled in Table 2:

TABLE 2

| Hydrogenation Temperature °C. | Gas-Chromatographic Analysis of Distillate (*) (%) | | | | Ester Conversion of 2nd Stage () (%) | Yield (*) (%) |
|---|---|---|---|---|---|---|
| | NPG | MB-NPG | TMP | Residual Compounds | | |
| 170 | 98.1 | 1.4 | 0.2 | 0.3 | 75.0 | 99.9 |
| 180 | 99.2 | 0.6 | 0.2 | 0.0 | 89.3 | 99.5 |
| 190 | 99.1 | 0.7 | 0.2 | 0.0 | 87.5 | 95.5 |
| 200 | 99.5 | 0.5 | 0.0 | 0.0 | 91.1 | 68.7 |

(*), (), (*), see above.

These results demonstrate that by means of the process of this invention the reduction of MB-NPG is accomplished at temperatures which are considerably lower (namely around 180° C.) than indicated in the literature (200°–220° C., see above), and that at these temperatures an excellent yield is obtained.

Furthermore, the hydrogenation test conducted at 200° C. proves that in spite of strong decomposition (lower yield), no by-products are formed which contaminate the distilled NPG, but that, on the contrary, a product of extreme purity is obtained. This result is in opposition to the statements in DAS [German Published Application] No. 2,054,601 (see above) that it is impossible to hydrogenate hydroxypivalaldehyde in the liquid phase without the formation of undesirable by-products, which would lessen the purity of the diol.

COMPARATIVE EXAMPLE 1

Since, in the literature, nickel catalysts are frequently proposed for the hydrogenation of hydroxypivalaldehyde, a comparative experiment has been conducted with a nickel catalyst having the following chemical composition:

| | |
|---|---|
| Ni (as the formate) | 10-11% |
| Cu | about 3% |
| Cr | about 0.2% |
| $SiO_2$ | about 65% |
| drying loss | about 1% |

The starting compound is product B described in Example 1. The hydrogenation reactor utilized (length 930 mm, diameter 45 mm) has an effective volume of 1.4 liters and is filled with 1,300 ml of the above-mentioned catalyst. The amount of waste gas is set at 400 liters per hour and the amount of starting material at 100 ml per hour (charge of 0.08). The hydrogen pressure is 300 bar.

To hydrogenate under maximally gentle conditions, a temperature of 120° C. is initially employed. Since the hydrogenation product has a carbonyl number of 2.7, i.e., the aldehydes are not completely hydrogenated, the temperature is gradually raised. Even at 160° C., however, the carbonyl number is still above 2, and the saponification number of the isobutanol-containing solution is above 59.

Thereafter, the hydrogenation product is once again passed over the catalyst under the same conditions. During this step, the carbonyl number drops from about 2 to 0.1, but the saponification number is only slightly reduced (from 59 to 54).

This twice-hydrogenated product is examined in greater detail in a sample distillation. During distillation, a distillation residue is obtained which is more than twice as large (exact factor: 2.10) as compared with the hydrogenation using the catalyst employed in Example 2 (see Example 2.1), i.e. during hydrogenation, high-boiling products have been formed.

A rehydrogenation at 180° C. over the catalyst used in Example 2, in the manner described in Comparative Example 2, merely leads to a reduction of the saponification number from 54 to 33. The hydrogenation product of this experiment results, with a further rehydrogenation under the same conditions (180° C., catalyst as used in Example 2), in a reduction of the saponification number from 33 to 18. A saponification number of 18 would correspond to an ester content of at least 13.9% (if, for the sake of simplicity, all esters are calculated as being MB-NPG), based on solid matter. Thus, this value is much too high.

If, in the first stage, hydrogenation is carried out with the barium-activated copper chromite catalyst used in Example 2 at temperatures of above 160° C., for example 180° C., yields of less than 90%, which are too low, are obtained and, in the second stage, a higher proportion of by-products results. The degree of purity of the thus-obtained NPG is below 98%.

These results show very clearly that the hydrogenation in the second stage can be conducted satisfactorily only if the starting product has been prehydrogenated in the first stage in accordance with this invention.

COMPARATIVE EXAMPLE 2

(Relating to the Second Stage)

To examine the hydrogenating capacity of the extensively anhydrous MB-NPG, a mixture of compounds is prepared by partial esterification of pure NPG with isobutyric acid, which mixture contains only NPG and MB-NPG. This product is diluted with such an amount of isobutanol that a 40% strength solution is obtained. The ester content of this solution is 6.3% (=15.9%, based on solid matter) and the water content is merely 0.3%.

The solution is hydrogenated at 170° C. and 180° C. over the catalyst used in Example 2 (1107 T by HARSHAW) at 300 bar hydrogen pressure. The hydrogenation reaction (length 60 cm, diameter 16 mm) has an effective volume of 110 ml and is filled with 100 ml of the above-mentioned catalyst. The amount of waste gas is set at 200 l. and the quantity of starting material at 20 ml per hour.

Samples are taken from the hydrogenation products and distilled, in order to conduct exact analyses by gas chromatography. The results of the two experiments are shown in Table 3:

TABLE 3

| Hydrogenation Temperature °C. | Gas-Chromatographic Analysis of Distillate (%) | | | Ester Conversion (%) | Yield (%) |
|---|---|---|---|---|---|
| | NPG | MB-NPG | Residual Compounds | | |
| 170 | 99.3 | 0.5 | 0.2 | 96.9 | 72.9 |
| 180 | 99.4 | 0.4 | 0.2 | 97.5 | 72.3 |

These results demonstrate that in the case of an extensively anhydrous starting material, even at relatively low temperatures, a vigorous decomposition takes place (lower yield), but that yet, contrary to the viewpoint expressed in DAS No. 2,054,601, the formation of by-products lessening the purity of NPG is not observed. The ester conversion is surprisingly the higher, the lower the water content.

If the above-described experiments are conducted under the same conditions but, according to this invention, with the addition of, for example, 6% water (based on the solution), then the NPG yield is increased to above 98%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of neopentyl glycol consisting essentially of
   reacting isobutyraldehyde, formalin and an aldol condensation catalyst to form a crude hydroxypivalaldehyde, containing the monoisobutyric acid ester of NPG as an impurity;
   high-pressure hydrogenating the crude hydroxypivalaldehyde obtained directly as the non-aqueous phase product thereof in the liquid phase over a barium-activated copper chromite catalyst, in the presence of 3-8% of water, and in two stages wherein, in the first stage, the temperature is 120°-160° C. and the charge of hydrogenation starting materials is 0.05-1.0 liter/liter of catalyst.h, and in the second stage, the temperature is 170°-200° C. and the charge of hydrogenation starting material is 0.05-1.0 liter/liter of catalyst.h, whereby there is obtained neopentyl glycol having a degree of purity of above 98% as determined by gas chromatographic analysis.

2. The process of claim 1, wherein the hydrogenation is carried out in the first stage at a temperature of 140°-150° C. and in the second stage at a temperature of 175°-190° C.

3. The process of claim 1, wherein the hydrogenation is carried out in both stages at a charge of 0.1-0.5 liter of hydrogenation starting material/liter of catalyst.h.

4. The process of claim 1, wherein the crude hydroxypivaladehyde has a water content of 3-8%.

5. The process of claim 1 wherein the hydrogenation is carried out in both stages under a hydrogen pressure of 200-300 bar.

6. A process for the production of neopentyl glycol consisting essentially of high-pressure hydrogenating a crude hydroxypivalaldehyde, containing the monoisobutyric acid ester of NPG as an impurity, the crude hydroxypivalaldehyde being obtained directly as the non-aqueous phase product of reacting isobutyraldehyde, formalin and an aldol condensation catalyst, the hydrogenating being carried out in the liquid phase over a barium-activated copper chromite catalyst, in the presence of 3-8% of water, and in two stages wherein, in the first stage, the temperature is 120°-160° C. and the charge of hydrogenation starting material is 0.05-1.0 liter/liter of catalyst.h, and in the second stage, the temperature is 170°-200° C. and the charge of hydrogenation starting material is 0.05-1.0 liter/liter of catalyst.h, whereby there is obtained neopentyl glycol having a degree of purity of above 98% as determined by gas chromatographic analysis.

* * * * *